(12) United States Patent
Zhan et al.

(10) Patent No.: US 6,798,511 B1
(45) Date of Patent: Sep. 28, 2004

(54) IMAGING ELLIPSOMETRY

(75) Inventors: Qiwen Zhan, Lauderdale, MN (US); James R. Leger, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 223 days.

(21) Appl. No.: 09/691,006

(22) Filed: Oct. 18, 2000

(51) Int. Cl.[7] .................................................. G01J 4/00
(52) U.S. Cl. ...................................................... 356/369
(58) Field of Search ................................. 356/364–369; 250/372, 225

(56) References Cited

U.S. PATENT DOCUMENTS

| | | | |
|---|---|---|---|
| 4,893,932 A | | 1/1990 | Knollenberg |
| 5,022,743 A | * | 6/1991 | Kino et al. .................. 350/507 |
| 5,042,951 A | | 8/1991 | Gold et al. |
| 5,133,601 A | | 7/1992 | Cohen et al. |
| 5,159,412 A | * | 10/1992 | Willenborg et al. ........ 356/445 |
| 5,181,080 A | | 1/1993 | Fanton et al. |
| 5,204,734 A | | 4/1993 | Cohen et al. |
| 5,220,403 A | | 6/1993 | Batchelder et al. |
| 5,359,622 A | | 10/1994 | Shih |
| 5,486,701 A | | 1/1996 | Norton et al. |
| 5,521,705 A | | 5/1996 | Oldenbourg et al. |
| 5,602,643 A | * | 2/1997 | Barrett ........................ 356/495 |
| 5,602,820 A | | 2/1997 | Wickramasinghe et al. |
| 5,754,296 A | | 5/1998 | Law |
| 5,822,073 A | | 10/1998 | Yee et al. |
| 5,910,841 A | | 6/1999 | Masao |
| 5,939,709 A | * | 8/1999 | Ghislain et al. ............ 250/216 |
| 5,963,326 A | | 10/1999 | Masao |
| 5,991,488 A | | 11/1999 | Salamon et al. |
| 6,008,892 A | * | 12/1999 | Kain et al. .................. 356/246 |
| 6,127,183 A | | 10/2000 | Ivarsson et al. |
| 6,177,990 B1 | * | 1/2001 | Kain et al. .................. 356/246 |
| 6,404,544 B1 | * | 6/2002 | Kuhn .......................... 359/371 |
| 6,493,097 B1 | | 12/2002 | Ivarsson |
| 6,594,011 B1 | | 7/2003 | Kempen |

OTHER PUBLICATIONS

Azzam, "Differential reflection phase shift under conditions of attenuated internal reflection," *J. Opt. Soc. Am. A*, 1999;16(7):1700–1702.

Bu–Abbud et al., "Characterization of Fabrication Damage in SrTiO$_3$ by Internal and External Measurements," *Surface Science*, 1980;96:329–345.

Burshta et al., "Ellipsometry of guided wave polaritons at solid surfaces," *Surface Science*, 1994;301:399–404.

(List continued on next page.)

*Primary Examiner*—Hoa Q. Pham
(74) *Attorney, Agent, or Firm*—Mueting, Raasch & Gebhardt, P.A.

(57) ABSTRACT

An ellipsometer apparatus and method for use in providing an image of at least a portion of a sample includes an objective lens having a focal plane at which a sample plane of a sample is positioned. Linearly polarized light normal to the sample plane incident on the objective lens is provided, and the incident linearly polarized light is focused onto the sample. At least a portion of the focused incident polarized light is reflected by the sample resulting in reflected light. Spatial filtering is used to modify at least a portion of the incident or the reflected light. An analyzer portion is operable to generate polarization information based on the reflected light.

44 Claims, 8 Drawing Sheets

OTHER PUBLICATIONS

Ikeda et al., "Molecular orientation near the surface of a smectic liquid crystal cell showing V–shaped switching by means of attenuated total internal reflection ellipsometry," *Physical Review E*; 2001;63:061703–1–7.

Irene, "Ultra–thin $SiO_2$ film studies: index, thickness, roughness and the initial oxidation regime," *Solid State Electronics*, 2001;45:1207–1217.

Johansen et al., "Imaging surface plasmon resonance sensor based on multiple wavelengths: Sensitivity considerations," *Review of Scientific Instruments*, 2000;71(9):3530–3538.

Moy, "Immersion ellipsometry," *Applied Optics*, 1981;20(22):3821–3822.

Pokrowsky, "Optical methods for thickness measurements on thin metal films," *Applied Optics*, 1991;30(22):3228–3232.

Takabayashi et al., "Propagation length of guided waves in lossy Si film sandwiched by identical dielectrics," *J. Opt. Soc. Am. B*, 1995;12(12):2406–2411.

Tiwald et al., "Determination of the mid–IR optical constants of water and lubricants using IR ellipsometry combined with an ATR cell," *Thin Solid Films*, 1998;313–314:718–721.

Yablonskii et al., "Control of the bias tilt angles in nematic liquid crystals," *J. Appl. Phys.*, 1999;85(5):2556–2561.

Zhan et al., "High–Resolution Imaging Ellipsometer", *Applied Optics*, 2002; 41(22):4443–4450.

Zhan et al., "Near–Field Nano–Ellipsometer for Ultrathin Film Characterization", *Journal of Microscopy*, 2003;210:214–219.

Zhan, "Novel Polarization Measurement and Manipulation Techniques for Nanometer Scale Applications", Thesis, University of Minnesota, August 2002; title pages, Acknowledgement, Abstract, and Table of Contents only:12 pp.

Zhan, "Radiation Forces on a Dielectric Sphere Produced by Highly Focused Cylindrical Vector Beams", *Journal of Optics A: Pure and Applied Optics*, 2003; 5:229–232.

Absolute Ellipsometry (AE). Therma–Wave Measurement Technologies [retrieved from the Internet on Feb. 11, 2003]. http://thermawave.com/technology/ae.htm., 1 p.

Ashkin, "History of optical trapping and manipulation of small–neutral particle, atoms and molecules," *IEEE Journal on selected topics in Quantum Electronics*, 2000; 6:841–856.

Beijerbergen, et al., "Helical–wavefront laser beams produced with a spiral phaseplate," *Optics Comm.*, 1994; 112:321–327.

Berger et al., "Resolution in surface plasmon microscopy," *Rev. Sci. Instrum.*, 1994; 65:2829–2836.

Biss et al., "Cylindrical vector beam focusing through a dielectric interface," *Optics Express*, 2001; 9:490–497.

Courtial et al., "Rotational frequency shift of a light beam," *Phys. Rev. Lett.*, 1998; 81:4828–4830.

DUV Spectroscopic Ellipsometry (SE). Therma–Wave Measurement Technologies [retrieved from the Internet on Feb. 11, 2003]. http://www.thermawave.com/technology/duvse.htm. 1 p.

Goodman, Introduction to Fourier Optics, 2d ed., New York, 1996; cover page, title page and table of contents, 8 pp.

Gu (editor), *Advanced Optical Imaging Theory*, Springer Series in Optical Sciences, New York, 2000, 8 pp.

Hafizi et al., "Laser–driven acceleration with Bessel beams," *Phys. Rev. E*, 1997; 55:3539–3545.

Harada et al., "Radiation forces on a dielectric sphere in the Rayleigh scattering regime," *Optics Comm.*, 1996; 124:529–541.

He et al., "Direct observation of transfer of angular momentum to absorptive particles from a laser beam with a phase singularity," *Phys. Rev. Lett.*, 1995; 75:826–829.

Hsieh et al., "Image contrast in polarization microscopy of magneto–optical disk data–storage media through birefringent plastic substrates," *Appl. Opt.*, 1997; 36:4839–4852.

Kano et al., "Excitation of surface–plasmon polaritons by a focused laser beam," *J. Opt. Soc., Am. B*, 1998; 15:1381–1386.

Kuga et al., "Novel optical trap of atoms with a doughnut beam," *Phys. Rev. Lett.*, 1997; 78:4713–4716.

Liu et al., "Vector diffraction from subwavelength optical disk structures: two–dimensional modeling of near–field profiles, far–field intensities, and detector signals from a DVD," *Appl. Opt.*, 1999; 38:3787–3797.

Mansuripur, *The physical principles of magneto–optical recording*, Cambridge, Mass. 1995; cover page, title page, table of contents, 10 pp.

Minhas et al., "Ellipsometic scatterometry for the metrology of sub–0.1–$\mu$m–linewidth structures," *Appl. Opt.*, 1998; 37:5112–5115.

Mirotznik et al., "Three–dimensional vector–based analysis of sub–wavelength diffractive optical elements using the finite–difference time–domain (FDTD) method," Diffractive Optics and Micro–Optics, vol. 10; 1998; OSA Technical Digest Series (Optical Society of America, Washington, D.C.); 91–93.

Mirotznik et al., "A hybrid finite element–boundary element method for the analysis of diffractive elements," *J. Mod. Opt.*, 1996; 43:1309–1321.

Moharam et al., "Diffraction analysis of dielectric surface–relief gratings," *J. Opt. Soc. Am.*, 1982; 72:1385–1392.

Moharam et al., "Formulation for stable and efficient implementation of the rigorous coupled–wave analysis of binary gratings," *J. Opt. Soc. Am. A*, 1995; 12:1068–1076.

Moharam et al., "Stable implementation of the rigorous coupled–wave analysis for surface–relief gratings: enhanced transmittance matrix approach," *J. Opt. Soc. Am. A*, 1995; 12:1077–1086.

Niziev et al., "Influence of beam polarization on laser cutting efficiency," *J. Phys. D*, 1999; 32:1455–1461.

Oron et al., "Efficient formation of pure helical laser beams," *Optics Comm.*, 2000; 182:205–208.

Oron et al., "The formation of laser beams with pure azimuthal or radial polarization," *Appl. Phys. Lett.*, 2000; 77:3322–3324.

Otaki et al., "Polarization effect on signal from optical ROM using solid immersion lens," *Jpn. J. Appl. Phys.*, 2000; 39:698–706.

Paesler et al, "Optical Tunneling Microscopes," *Near–Field Optics, Theory, Instrumentation, and Applications*, New York, New York, 1996, 143–161.

Prather et al., "Formulation and application of the finite–difference time–domain method for the analysis of axially symmetric diffractive optical elements," *J. Opt. Soc. Am. A*, 1999; 16:1131–1142.

Quabis et al., "The focus of light–theoretical calculation and experimental tomographic reconstruction," *Appl. Phys. B*, 2001; 71:109–113.

Raether, "Surface plasmons on smooth and rough surfaces and on gratings," Spinger–Verlag, Berlin, 1988. cover page, title page, table of contents, 4 pp.

Richards et al., "Electromagnetic diffraction in optical systems II. Structure of the image field in an aplanatic system," *Proc. R. Soc. London Ser. A*, 1959; 253:358–379.

Rothenhäusler et al., "Surface–plasmon microscopy," *Nature*, 1998; 332:615–617.

Sato et al., "Optical trapping of microscopic metal particles," *Opt. Lett.*, 1994; 19:1807–1809.

Somekh et al., "Optical V(z) for high resolution $2\pi$ surface plasmon microscopy," *Opt. Lett.*, 2000; 25:823–825.

Stalder et al., "Linearly polarized light with axial symmetry generated by liquid–crystal polarization converters," *Opt. Lett.*, 1996; 21:1948–1950.

Taflove, *Computational Electrodynamics—The Finite–Difference Time–Domain Method*, Boston, Mass., 1995; cover page, title page, table of contents, 13 pp.

Tominaga et al., "Local plasmon photonic transistor," *Appl. Phys. Lett.*, 2001; 78:2417–2419.

Tompkins, *A user's guide to ellipsometry*, Boston, Mass. 1993; cover page, title page, table of contents, 9 pp.

Wang et al. "Measuring and modeling optical diffraction from subwavelength features," *J. Opt. Soc. Am. A*, 2001; 18(3):565–572.

Wolf, "Electromagnetic diffraction in optical systems I. An integral representation of the image field," *Proc. R. Soc. Ser. A*, 1959; 253:349–357.

Wu et al., "Realization of numerical aperture 2.0 using a gallium phosphide solid immersion lens," Applied Physics Letters, Dec. 27, 1999; 75(26):4064–4066.

Youngworth et al., "Focusing of high numerical aperture cylindrical vector beams," *Optics Express*, 2000; 7:77–87.

Zhan et al., "Focus shaping using cylindrical vector beams," *Optics Express*, Apr. 8, 2002; 10(7):324–331.

Zhan et al., Imaging ellipsometry for high–spatial–resolution metrology, University of Minnesota, Minneapolis, MN, SPIE Proceedings, vol. 4435, Wave optics and VLSI photonic devices for information processing, 2001; 65–76.

Zhan et al., "Interferometric measurement of the geometric phase in space–variant polarization manipulations," *Optics Communications*, 2002; 213:241–245.

Zhan et al., "Measurement of surface features beyond the diffraction limit using an imaging ellipsometer," *Optics Letters*, May 15, 2002; 27(10):821–823.

Albersdorfer et al., "High resolution imaging microellipsometry of soft surfaces at 3 $\mu$m lateral and 5 Å normal resolution", *Appl. Phys. Lett.*, 72(23):2930–2932 (1998).

Azzam et al., "Ellipsometry and Polarized Light", Amsterdam, North Holland Physics Publishing (1988).

Beam Profile Ellipsometry (BPE). Therma–wave [retrieved on Jan. 15, 2001]. Retrieved from the Internet: <URL: http://www.thermawave.com/technology/bpe.htm>, 1 p.

Chou et al., "Subwavelength amorphous silicon transmission gratings and applications in polarizers and waveplates", *Appl. Phys. Lett.*, 67(6):742–744 (1995).

Cohn et al., "Dynamic imaging microellipsometry: theory, system design, and feasibility demonstration", *Applied Optics*, 27(22):4664–4671 (1988).

Erman et al., "Spatially resolved ellipsometry", *J. Appl. Phys.*, 60(3):859–873 (1986).

Jin et al., "Imaging ellipsometry revisited: Developments for visualization of thin transparent layers on silicon substrates", *Rev. Sci. Instrum.*, 67(8):2930–2935 (1996).

I–Elli2000 Imaging Ellipsometer. Nano–film Technologie [retrieved on Jan. 15, 2001]. Retrieved from Inernet: <URL: http:www.nanofilm.ed/html/elli2000/body_i–elli2000.html>, 16 pp.

Imaging Ellipsometer. Beaglehole Instruments [retrieved on Jan. 15, 2001]. Retrieved from Internet: <URL: http://www.beaglehole.com/imelli/im–main.html>, 9 pp.

Karlsson, "Detector and Data Acquisition System for an Imaging Ellipsometer", IEEE Instrumentation and Measurement Technology Conference, St. Paul, Minnesota, USA, May 18–21, 1998, 1:679–682 (1998).

Leng et al., "Characterization of titanium nitride (TiN) films on various substrates using spectrophotometry, beam profile reflectometry, beam profile ellipsometry and spectroscopic beam profile ellipsometry", *Thin Solid Films*, 313–314:308–313 (1998).

Leng et al., "Combined beam profile reflectometry, beam ellipsometry and ultraviolet–visible spectrophotometry for the characterization of ultrathin oxide–nitride–oxide films on silicon", *J. Vac. Sci. Tech.*, A17(2):380–384 (1999).

Liu et al., "Image scanning ellipsometry for measuring nonuniform film thickness profiles", *Applied Optics*, 33(7):1223–1229 (1994).

Logofatu et al., "Identity of the cross–reflection coefficients for symmetric surface–relief gratings", *J. Opt. Soc. Am. A*, 16(5):1108–1114 (1999).

Mansfield et al., "Solid immersion microscope", *Appl. Phys. Lett.*, 57(24):2615–2616 (1990).

Mansuripur, "Certain computational aspects of vector diffraction problems", *J. Opt. Soc. Am. A*, 6(5):786–805 (1989).

Mansuripur, "Distribution of light at and near the focus of high–numerical–aperture objectives", *J. Opt. Soc. Am. A*, 3(12):2086–2093 (1986).

Nordin et al., "Broadband form birefringent quarter–wave plate for the mid–infrared wavelength region", *Optics Express*, 5(8):163–168 (1999).

Rosencwaig et al., "Beam profile reflectometry: a new technique for dielectric film measurements", *Appl. Phys. Lett.*, 60(11):1301–1303 (1992).

See et al., "Scanning optical microellipsometer for pure surface profiling", *Applied Optics*, 35(34):6663–6668 (1996).

Spesivtsev et al., "Automatic Scanning Microellipsometer", *Optoelectr., Instrum. and Data Process.*, 1:90–94 (1997).

Tompkins et al., "Spectroscopic Ellipsometry and Reflectometry", N.Y., John Wiley & Sons, Inc. (1999).

Ye, "Non mechanical half–wave plate polarization rotator", *Optik*, 101(2):77–79 (1995).

\* cited by examiner

IMAGING ELLIPSOMETRY

FIELD OF THE INVENTION

The present invention relates to ellipsometry. More particularly, the present invention pertains to imaging ellipsometry.

BACKGROUND OF THE INVENTION

Ellipsometry is an optical technique that uses polarized light to probe the dielectric properties of a sample. The most common application of ellipsometry is the analysis of very thin films. Through the analysis of the state of polarization of the light that interacts with the sample, ellipsometry can yield information about such films. For example, depending on what is already known about the sample, the technique can probe a range of properties including the layer thickness, morphology, or chemical composition.

Generally, optical ellipsometry can be defined as the measurement of the state of polarized light waves. An ellipsometer measures the changes in the polarization state of light when it interacts with a sample. The most common ellipsometer configuration is a reflection ellipsometer, although transmission ellipsometers are sometime used. If linearly polarized light of a known orientation is reflected or transmitted at oblique incidence from a sample surface, then the resultant light becomes elliptically polarized. The shape and orientation of the ellipse depend on the angle of incidence, the direction of the polarization of the incident light, the wavelength of the incident light, and the Fresnel properties of the surface. The polarization of the light is measured for use in determining characteristics of the sample. For example, in one conventional null ellipsometer, the polarization of the reflected light can be measured with a quarter-wave plate followed by an analyzer. The orientation of the quarter-wave plate and the analyzer are varied until no light passes though the analyzer, i.e., a null is attained. From these orientations and the direction of polarization of the incident light, a description of the state of polarization of the light reflected from the surface can be calculated and sample properties deduced.

Two characteristics of ellipsometry make its use particularly attractive. First, it is a nondestructive technique, such that it is suitable for in situ observation. Second, the technique is extremely sensitive. For example, it can measure small changes of a film down to sub-monolayer of atoms or molecules. For these reasons, ellipsometry has been used in physics, chemistry, materials science, biology, metallurgical engineering, biomedical engineering, etc.

As mentioned above, one important application of ellipsometry is to study thin films, e.g., in the fabrication of integrated circuits. In the context of ellipsometry, a thin film is one that ranges from essentially zero thickness to several thousand Angstroms, although this range can be extended in many cases. The sensitivity of an ellipsometer is such that a change in film thickness of a few Angstroms can usually be detected. From the measurement of changes in the polarization state of light when it is reflected from a sample, an ellipsometer can measure the refractive index and the thickness of thin films, e.g., semi-transparent thin films. The ellipsometer relies on the fact that the reflection at a material interface changes the polarization of the incident light according to the index of refraction of the interface materials. In addition, the polarization and overall phase of the incident light is changed depending on the refractive index of the film material as well as its thickness.

Generally, for example, a conventional reflection ellipsometer apparatus, such as shown in FIG. 1, includes a polarizer arm 12 and an analyzer arm 14. The polarizer arm 12 includes a light source 14 such as a laser (commonly a 632.8 nm helium/neon laser or a 650–850 nm semiconductor diode laser) and a polarizer 16 which provides a state of polarization for the incident light 18. The polarization of the incident light may vary from linearly polarized light to elliptically polarized light to circularly polarized light. The incident light 18 is reflected off the sample 10 or layer of interest and then analyzed with the analyzer arm 14 of the ellipsometer apparatus. The polarizer arm 12 of the ellipsometer apparatus produces the polarized light 18 and orients the incident light 18 at an angle with respect to a sample plane 11 of the sample 10 to be analyzed, e.g., at some angle such as 20 degrees with respect to the sample plane 11 or 70 degrees with respect to the sample normal.

The reflected light 20 is examined by components of the analyzer arm 14, e.g., components that are also oriented at the same fixed angle with respect to the sample plane 11 of the sample 10. For example, the analyzer arm 14 may include a quarter wave plate 22, an analyzer 24 (e.g., a polarizer generally crossed with the polarizer 16 of the polarizer arm 12), and a detector 26. To measure the polarization of the reflected light 20, the operator may change the angle of one or more of the polarizer 16, analyzer 24, or quarter wave plate 22 until a minimal signal is detected. For example, the minimun signal is detected if the light 20 reflected by the sample 10 is linearly polarized, while the analyzer 24 is set so that only light with a polarization which is perpendicular to the incoming polarization is allowed to pass. The angle of the analyzer 24 is therefore related to the direction of polarization of the reflected light 20 if the minimum condition is satisfied. The instrument is "tuned" to this null (e.g., generally automatically under computer control), and the positions of the polarizer 16, the analyzer 24, and the incident angle 13 of the light relative to the sample plane 11 of the sample 10 are used to calculate the fundamental quantities of ellipsometry: the so called Psi, delta ($\Psi$, $\Delta$) pair given by:

$$\frac{r_p}{r_s} = \tan\Psi(e^{j\Delta})$$

where $r_p$ and $r_s$ are the complex Fresnel reflection coefficients for the transverse magnetic and transverse electrical waves of the polarized light, respectively. From the ellipsometry pair ($\Psi$, $\Delta$), the film thickness (t) and index of refraction (n) can be determined. It will be recognized that various ways of analyzing the reflected light may be possible. For example, one alternative is to vary the angle of the quarter wave plate and analyzer to collect polarization information.

Although many different types of ellipsometers exist, they have various shortcomings. For example, many are not suitable for characterizing samples that have very small transverse features. The smallest spot a conventional ellipsometer can measure is determined by the beam size, usually on the order of hundreds of microns. This essentially limits its application to samples with large and uniform interface characteristics. Resolution of an image produced by imaging ellipsometers is typically inadequate and improvement is necessary.

Advances in microelectronic fabrication are rapidly surpassing current capabilities and metrology. In order to enable future generations of microelectronics, some specific metrology capabilities must be developed. One of the key challenges is to measure the properties of complex layers of extremely thin films or submicron lateral dimensions.

Several systems have been developed to attack the above shortcomings. For example, to resolve the suitability of ellipsometers to characterize samples that have small transverse features, a microscope objective lens in a conventional ellipsometer has been used. For example, the microscope objective lens has been the basis for several ellipsometry methods including spatially resolved ellipsometry (SRE), image scanning ellipsometry (ISE), and dynamic imaging micro-ellipsometry (DIM). However, such methods and systems also have drawbacks.

With respect to spatially resolved ellipsometry, such techniques can measure small features, but they are typically too time consuming for many applications because the sample has to be measured point by point. Such a time consuming process makes this system highly undesirable for many applications.

With respect to ellipsometry systems that perform image scanning ellipsometry and dynamic imaging micro-ellipsometry, such systems usually use an imaging apparatus in an arm of a conventional ellipsometer to image the sample at a large incident angle. Such systems lead to different magnifications in two directions, which result in a distortion of an image being produced. A scanning mechanism or other complicated optical system is thus required to correct such distortion. Further, the slant or incident angle of the light relative to the sample plane also limits the use of the highest numerical aperture objective lenses, which, in turn, limits the achievable resolution of such systems.

SUMMARY OF THE INVENTION

Imaging ellipsometry according to the present invention is presented which characterize a sample with high resolution. The imaging ellipsometry described herein can perform accurate measurements with high speed and high resolution using a very simplified apparatus. Generally, to achieve high resolution and form an image, an objective lens (e.g., a high numerical aperture objective lens) is used. Polarization effects due to Fresnel reflection with a high numerical aperture objective lens are used as a measurement signal in the imaging ellipsometry according to the present invention.

An ellipsometry apparatus according to the present invention includes an objective lens having a focal plane at which a sample plane of a sample is positioned. An illumination source provides incident light normal to the sample plane. The incident light includes linearly polarized light incident on the objective lens. The objective lens focuses the incident light onto the sample. At least a portion of the focused incident polarized light is reflected by the sample resulting in reflected light. A spatial filter modifies at least a portion of the incident light and the reflected light. An analyzer portion is used to generate polarization information based on the reflected light.

In various embodiments of the apparatus, the illumination source may be a fiber illuminator, the objective lens may be a high numerical aperture objective lens having a numerical aperture in the range of 0.5 to less than 1, and the spatial filter may be positioned adjacent the objective lens in an actual plane of the exit pupil thereof or may be positioned in a conjugate plane of the exit pupil of the objective lens.

In another embodiment of the apparatus, the analyzer portion includes a rotatable quarter wave plate, an analyzer, a lens, and a detector, e.g., a charge coupled device array detector. The rotatable quarter wave plate, the analyzer, and the lens are positioned such that the reflected light passes through the rotatable quarter wave plate and the analyzer. Further, the reflected light is focused onto the detector by the lens.

In another embodiment of the invention, the apparatus further comprises a beam splitter that passes the linearly polarized light normal to the focal plane and incident on the objective lens. Further, the beam splitter diverts the reflected light to the analyzer portion.

An ellipsometry method according to the present invention for use in providing an image of at least a portion of a sample is also described. The method includes providing an objective lens having a focal plane at which a sample plane of the sample is positioned. A linearly polarized light normal to the sample plane and incident on the objective lens is further provided. The incident linearly polarized light is focused onto the sample and at least a portion of the focused incident polarized light is reflected by the sample, resulting in reflected light. At least a portion of the incident light or the reflected light is spatially filtered and polarization information is generated based on the reflected light.

In one embodiment of the method, the linearly polarized light normal to the sample plane incident on the objective lens is provided by providing light from an extended source, collimating the light, and linearly polarizing the collimated light. In other embodiments of the method, the high numerical aperture objective lens may have a numerical aperture in the range of 0.5 to less than 1 and spatial filtering may use a spatial filter at an actual plane of an exit pupil of the objective lens or a spatial filter at a conjugate plane of an exit pupil of the objective lens In another embodiment of the method, the polarization information is generated by passing the reflected light through an analyzer portion comprising at least a rotatable quarter wave plate and an analyzer. At least the rotatable quarter wave plate is rotated to at least two angular positions. At least two polarization images corresponding to the at least two angular positions are detected.

In additional embodiments for the generation of polarization information, an image may be generated using a ratio or difference of the at least two polarization images. Further, the analyzer may also be rotated to one or more positions with corresponding additional polarization images being used for the generation of the polarization information.

In yet a further embodiment, the method may include providing the linearly polarized light normal to the sample plane incident on the objective lens with polarization states that are at ±45° with respect to an incident plane of the linearly polarized light using a polarization converter. Further, generation of the polarization information based on the reflected light may be performed using a polarization device matched to the polarization converter.

In yet another embodiment of the method, the spatial filtering may be provided by using a spatial filter configured such that the polarization state of the light that is modified thereby is aligned at 45° with respect to an incident plane of the linearly polarized light incident on the objective lens. In such an embodiment, the spatial filter may be synchronously rotated, with a rotatable quarter wave plate and an analyzer to generate a plurality of polarization images for use in generating polarization information.

Yet further, another embodiment of the method according to the present invention includes providing linearly polarized light by providing light such that an illumination line is focused on the sample. The illumination line is swept across the sample.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

Imaging ellipsometry according to the present invention shall be generally described with reference to FIG. 2. Thereafter, various illustrative embodiments of exemplary imaging ellipsometers and components thereof shall be described in further detail with reference to FIGS. 3–11.

Figure 1:
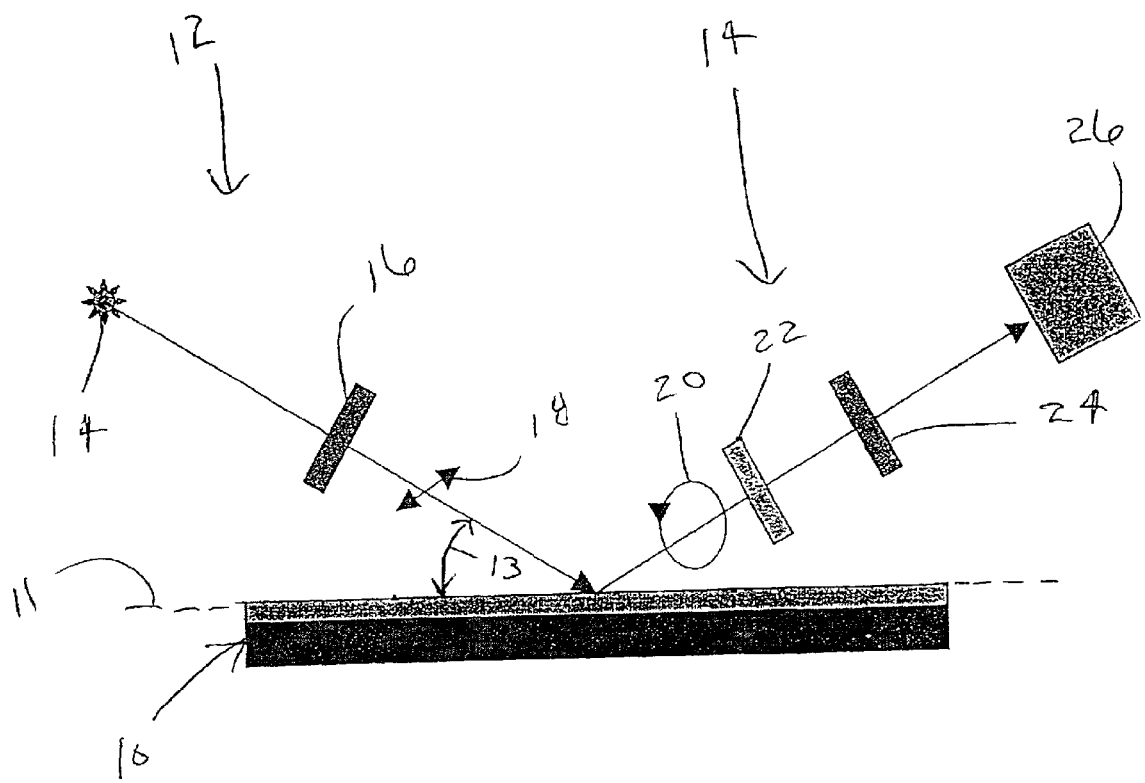
FIG. 1 shows a conventional reflection ellipsometer wherein incident light is provided at an oblique angle relative to the sample plane of a sample for reflection therefrom.
Figure 2:
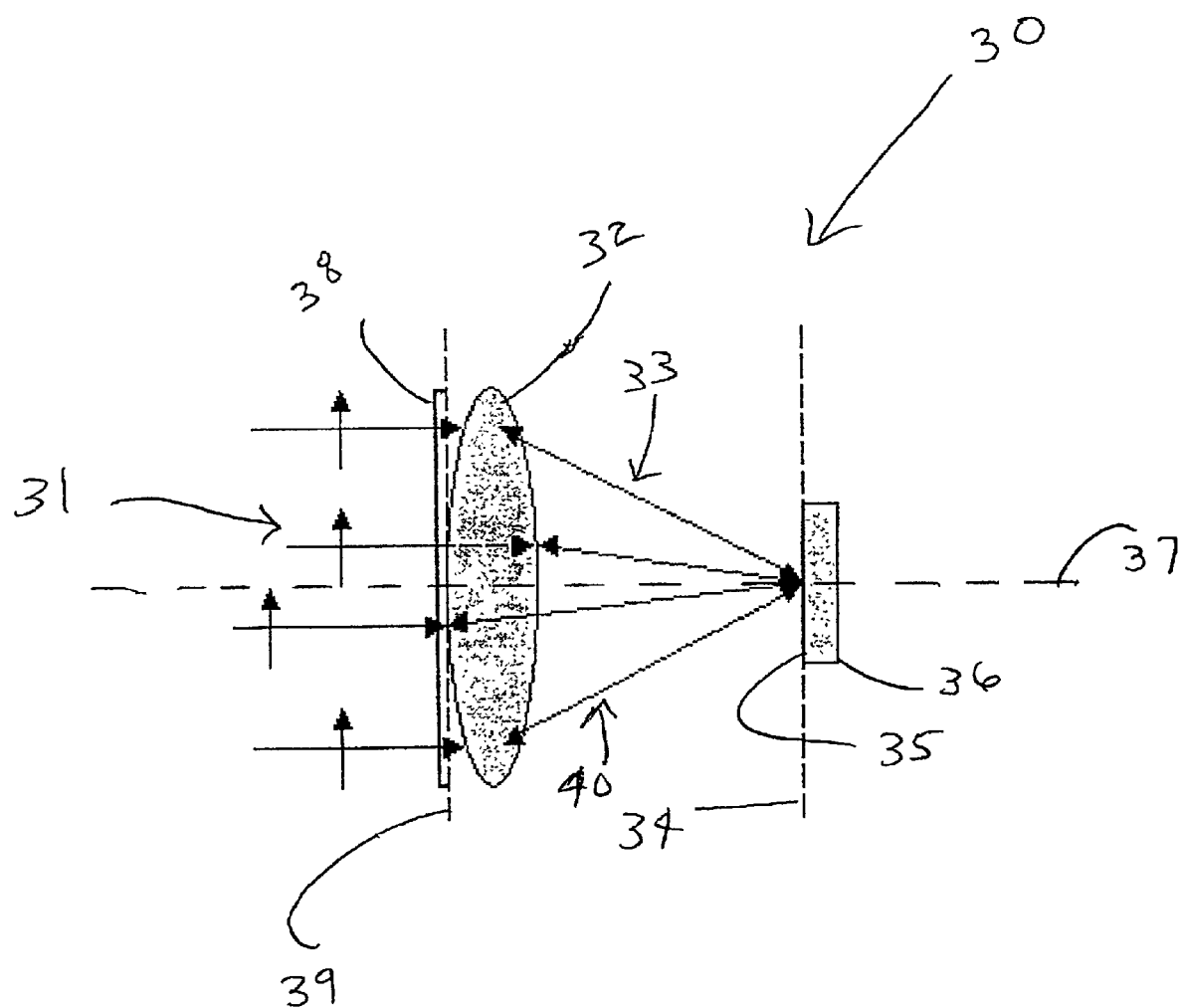
FIG. 2 is a general diagram illustrating imaging ellipsometry according to the present invention.

FIG. 2 shows an imaging ellipsometer apparatus 30 for use in forming an image, e.g., a high resolution image. An objective lens 32, e.g., a high numerical aperture objective lens, positioned orthogonal to and with its center on the optical axis 37, is used to focus linearly polarized light 31 onto a sample plane 35 of a sample 36 located at the focal plane 34 of the objective lens 32. In other words, the sample plane 35 and the focal plane 34 coincide. A sample plane 35 refers to a surface of the sample 36 to be analyzed. The incident light 31 is normal to the sample plane 35, i.e., the incident plane of the light is normal to the sample plane 35. The polarization effects due to the Fresnel reflection with the objective lens 32, e.g., a high numerical aperture objective lens, are used as a measurement signal in the imaging ellipsometer apparatus 30 according to the present invention.

An illumination source that illuminates the objective lens 32 provides the incident linearly polarized light 31 normal to the sample plane 35 and thus normal to objective lens 32 which is generally positioned in a parallel manner to sample plane 35. The objective lens 32 focuses such incident linearly polarized light 31 onto the sample 36. The focused incident light 33 is reflected, at least in part, as reflected light 40 and collected by the objective lens 32.

A suitable spatial filter 38 positioned in a plane 39 of the exit pupil of the objective lens 32, e.g., the actual plane 39 of the exit pupil or a conjugate plane of the exit pupil of the objective lens 32 as described further below, is used to extract phase information with regard to the polarization effects due to Fresnel reflection with the high numerical aperture objective lens 32. The spatial filter 38 which modifies the incident light 31 from the illumination source and/or the reflected light 40 is used with an analyzer apparatus (not shown in FIG. 2) such as a rotatable quarter wave plate and an analyzer in the path of the reflected light 40 to attain information about the sample 36.

Due to the symmetry of the phase distribution of the reflected light 40 in the absence of a spatial filter 38, the use of a spatial filter 38 is required according to the present invention. However, any suitable spatial filter 38 that modifies the light can be used. For example, a blocking spatial filter or a spatial filter that changes polarization state, such as a half wave plate, may be used to spatially filter the light according to the present invention.

By illuminating the objective lens 32 with incident light 31 from the illumination source having an incident plane normal to the sample plane 35, a high numerical aperture objective lens 32 may be used according to the present invention as the objective lens 32 is normal to the sample plane and can be positioned very close thereto. For example, at high numerical apertures, the objective lens 32 can be positioned within millimeters of the sample 36. As used herein, preferably, the high numerical aperture objective lens 32 has a numerical aperture in the range of 0.5 to less than 1. More preferably, the numerical aperture is in the range of 0.8 to less than 1. The higher the numerical aperture, the higher the resolution of an image produced according to the ellipsometry technique of the present invention. Further, the higher the numerical aperture, the stronger the ellipsometric signal provided for detection by the ellipsometry apparatus 30.

The ellipsometry apparatus 30 generally shown and described with reference to FIG. 2 can be extended to a variety of imaging ellipsometer configurations. Although many of these configurations are described herein with reference to FIGS. 3–11, such general concepts are not limited to only such imaging ellipsometer apparatus. Various other types of apparatus, such as those shown herein with additional components and/or component substitutions may also benefit from the concepts described herein as would be contemplated by one skilled in the art and in accordance with the scope of the appended claims.

Figure 3:
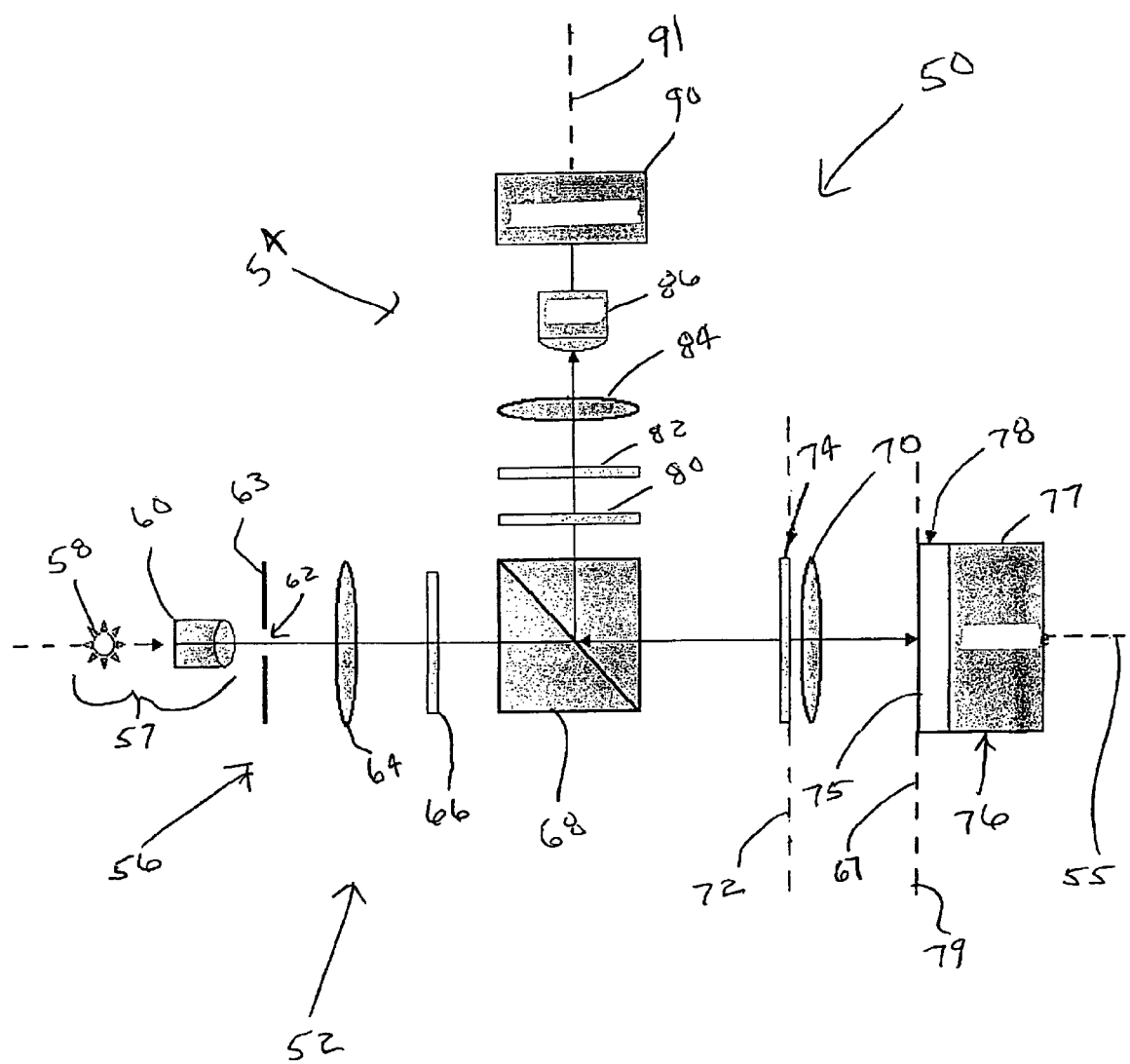
FIG. 3 is an illustrative diagram of one embodiment of an imaging ellipsometer apparatus using imaging ellipsometry as illustrated in FIG. 2 according to the present invention.

FIG. 3 is one illustrative diagram showing one exemplary embodiment of an imaging ellipsometer apparatus 50 according to the present invention. The imaging ellipsometer apparatus 50 includes a polarizer arm 52 and an analyzer arm 54. The polarizer arm 52 suitably aligned along optical axis 55 includes an illumination source 56 for providing collimated linearly polarized light for passage through beam splitter 68 and illumination of objective lens 70 after modification thereof by spatial filter 74. The objective lens 70 focuses the incident linearly polarized light from illumination source 56 onto thin film 78 of sample 76. The incident plane of the light illuminating the objective lens 70 is normal to a sample plane 75 of the film 78 positioned at the focal plane 79 of the objective lens 70.

Incident light reflected from the sample 76, i.e., reflected light, is collected by the objective lens 70 and recollimated thereby. The reflected light is then diverted by the beam splitter 68 to the analyzer arm 54.

The analyzer arm 54 includes a quarter wave plate 80, an analyzer 82, a lens 84, and a detector 86 aligned along optical axis 91. A computer apparatus 90 is used to process polarization information detected by detector 86 of the analyzer arm 54 to provide image information with respect to sample 76. The rotatable quarter wave plate 80, the analyzer 82, and the lens 84 are suitably positioned along the optical axis 91 such that the reflected light representative of image information which is diverted by the beam splitter 68 passes through the rotatable quarter wave plate and analyzer and is focused onto the detector 86 by the lens 84.

The sample 76 may be any structure that can be imaged according to the present invention. For example, the sample 76 may include a substrate portion 77 having thin film 78 provided thereon. Further, for example, the thin film 78 may be a silicon dioxide film, a multi-layer film, or any other thin films used in semiconductor fabrication processes. However, the present invention is not limited to use with semiconductor fabrication applications but may be important to other medical, material science, or biological science applications as well as any other imaging applications.

The illumination source 56 may include any elements suitable for providing incident linearly polarized light normal to the sample plane 75 of the sample 76 positioned at the focal plane 79 of the objective lens 70. For example, the light source may be of any suitable wavelengths and may be a laser beam or any other light source.

In the embodiment of the imaging ellipsometer apparatus 50 shown in FIG. 3, the illumination source 56 includes an extended light source, preferably a fiber illuminator including a light source 58 and a fiber bundle 60. One will recognize that a single spot source may also be used according to the present invention with corresponding imaging of a single spot. However, imaging of multiple spots is preferred using a fiber illuminator 57 as the illumination source 56.

In the illumination source 56, light from the fiber bundle 60 is provided to the collimating lens 64 via a pin hole opening 62 at the optical axis 55 in an aperture blocking structure 63. The pin hole opening 62 is used to limit the size of the field of view of the imaging ellipsometer apparatus 50. The pin hole opening 62 may be positioned such the structure 63 is in direct contact with the fiber bundle 60 or may be positioned a suitable distance therefrom. Plane 67 is representative of the image plane of the pin hole opening 62 and is located at the focal plane 79 of the objective lens 70.

The light from the fiber bundle 60 is collimated by the collimating lens 64 and linearly polarized by polarizer 66 of the illumination source 56 of the polarizer arm 52. Accordingly, the linearly polarized light from the illumination source 56 passes through beam splitter 68 and is modified by spatial filter 74, e.g., an aperture mask, prior to illumination of objective lens 70.

The spatial filter 74 is necessary to extract polarization information. Without a spatial filter 74, i.e., when the whole aperture is used, information on phase delay would be substantially zero because of the symmetry of the phase information regarding the reflected light from the sample 76. The spatial filter 74 is used to break the azimuth symmetry and allow for extraction of the phase delay information.

As used herein, a spatial filter is any filter that modifies a portion of the light in one region of the aperture relative spatially to light in another region thereof, whether the spatial filter is positioned in the analyzer arm or the polarizer arm of the imaging ellipsometer apparatus, e.g., blocking light in one region of the plane 72 of the exit pupil of the objective lens 70 relative to another region in the plane 72 of the exit pupil of the objective lens 70. Such modification may be performed in any number of ways. For example, light may be blocked in one region relative spatially to another region, the polarization state of light may be changed in one region relative spatially to another region, or any other spatial modification may be used.

Figure 7:
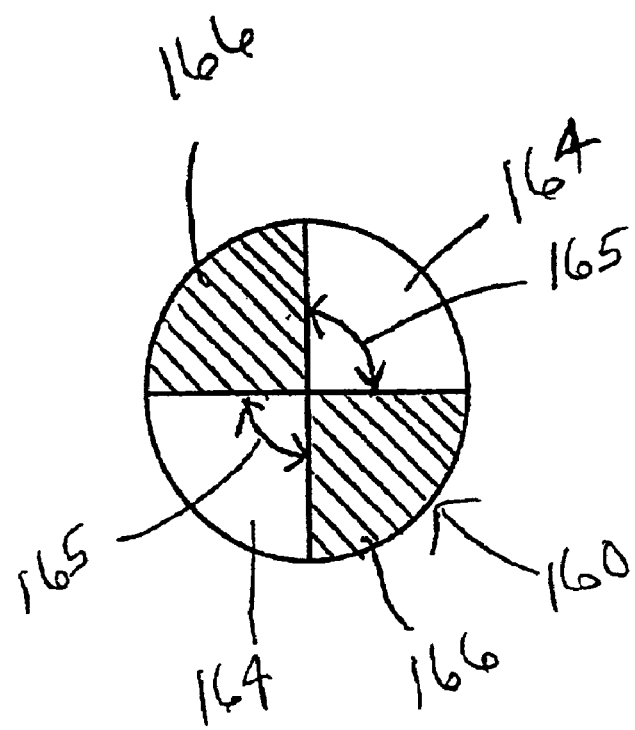
FIG. 7 is one illustrative embodiment of a spatial filter, e.g., an aperture mask, for use in an imaging ellipsometer apparatus according to the present invention.

One illustrative spatial filter 160 is graphically illustrated in FIG. 7 Spatial filter 160 is an aperture mask that blocks light in two opposite quadrants in the plane 72 of the exit pupil of the objective lens 70. As shown in FIG. 7, spatial filter 160 includes light blocking portions 166, e.g., two opposite quadrants, and light passing portions 164, e.g., two opposite quadrants.

When using the technique of blocking two opposite quadrants of the plane 72 of the exit pupil of the objective lens 70 according to the present invention, the non-uniformity of the illumination source, e.g., a fiber illuminator, in transverse dimensions may cause calibration problems with respect to the analysis of polarization information, e.g., calibration problems. Such a configuration may be optimized by selection of a desired angle 165, and thus the size of the regions passing and blocking light 164, 166. For example, the angle 165 may be chosen to maximize the ratio between the intensity signals output from the detector 86 during image capture at two different positions of the quarter wave plate, e.g., +/−45 degrees., in the analyzer arm 54 such that non-uniformity problems are reduced. For example, in one embodiment, the ratio of the signals is maximized by choosing an optimal aperture mask with the angle 165 being about 67°.

Figure 8:
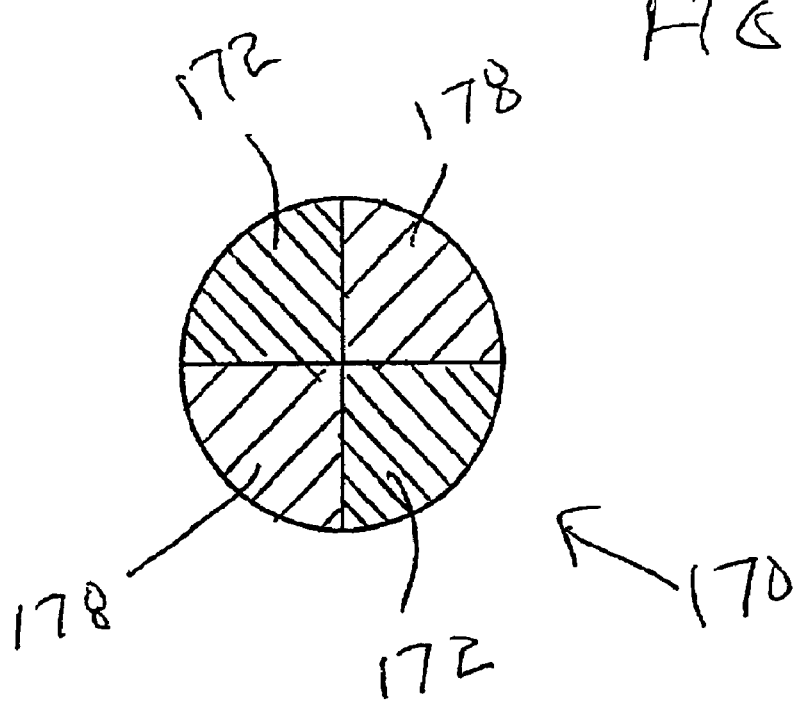
FIG. 8 is an alternate illustrative embodiment of a spatial filter for use in an imaging ellipsometer apparatus according to the present invention.

Another embodiment of a spatial filter 170 is shown in FIG. 8. Instead of blocking light in the two opposing quadrants in the plane 72 of the exit pupil of the objective lens 70, a patterned mask including half wave plates 172 at two opposite quadrants to modify the polarization state of the light passing therethrough and including two light passing portions 178, e.g., glass, at two opposite quadrants. The patterned mask is preferably designed such that the x-component of the light has an equal optical path in all four quadrants, while the y-component of the light has a half wavelength difference in optical path length between adjacent quadrants.

One skilled in the art will recognize that an unlimited number of different types of spatial filters may be used according to the present invention. As such, any spatial filter modifying one portion of the light in the plane 72 of the exit pupil of the objective lens 70 relative to another region in the plane 72 may be used according to the present invention. For example, more complicated masks or patterned designs consisting of patterned wave plates combined with light blocking filters may be used to further optimize detection.

With reflected light being collected by objective lens 70 and diverted by beam splitter 68 to analyzer arm 54, the analyzer arm 54 is used to capture images based on the intensity of the reflected light. The analyzer arm 54, which as shown in the embodiment of FIG. 3, includes at least the quarter wave plate 80, the analyzer 82, the lens 84, and the detector 86, preferably captures at least two polarization images at detector 86. For example, such images may be captured by rotating the quarter wave plate 80 to two different angular positions, e.g., ±45°, and capturing the images at such locations. Collection of more than two images allows for processing of such multiple images to attain higher resolution.

The analyzer 82 may include any polarization device for resolving the polarization state of the reflected light and providing such light for illumination of lens 84 which focuses the light representative of the image of the sample 76 on detector 86 positioned at the focal plane of the lens 84. Preferably, the polarizer 66 of the illumination source 56 and the analyzer 82 of the analyzer arm 54 are matched, or in other words are at a crossed position, i.e., 90°, relative to each other.

The detector 86 may include any light detection apparatus capable of detecting light intensity and providing polarization image signals therefrom based on such light intensity for processing by computer apparatus 90. Preferably, the detector 86 is a charge coupled device (CCD) array detector. Alternatively, the detector 86 could be a CMOS light detector. For example, the imaging may be performed with a high speed CCD camera with the adjustable imaging optics. With the use of a high speed frame grabber, rapid transfer of polarization images from the CCD detector 86 to the computer apparatus 90 may be accomplished with the computer apparatus 90 operable to process the polarization image data to calculate the final ellipsometry image.

In one embodiment of the imaging ellipsometer apparatus of FIG. 3, a polarization image is generated by preferably generating two polarization images, i.e., frames, at different angular positions of the quarter wave plate 80 of the analyzer arm 54. For example, by rotating the quarter wave plate 80 to ±45°, two polarization images can sequentially be captured by the CCD detector 86 and signals representative thereof are provided to the computer 90 for analysis thereby.

The polarization images captured by the CCD detector, e.g., pixel information representative of polarization information based on the intensity of the reflected light received at the detector 86, is used by the computer to generate ellipsometry images regarding the sample 76. For example, the polarization information associated with the pixels of the detector may be used by a computer program running on computer 90 to correlate polarization information, e.g., light intensity, with thickness of films.

For example, in one embodiment, the polarization information, e.g., light intensity, detected for pixels of the image can be correlated to the film thickness (t) and/or index of refraction (n) with use of a look-up table in memory of computer apparatus 90. In other words, a computer program (e.g., a simulation program) may be used to generate light intensities (e.g., I1 and I2, where I1 and I2 are the intensities for different orientations of the quarter wave plate 80) for various indices and thickness. The results can be stored in a look-up table in computer memory of the computer apparatus 90. When the light intensity is measured for a sample 76, the computer apparatus 90 can be used to search the look-up table and do an interpolation and regression computation to find film thickness (t) and/or index of refraction (n) corresponding to the polarization information, e.g., light intensity, captured by the detector 86. From the polarization images captured by the CCD detector 86, ellipsometric high resolution maps of the sample 76 may be generated therefrom, e.g., thickness can be used as a z-axis component in the map for x-axis/y-axis pixel locations.

In one preferred embodiment, two images are captured at two different quarter wave plate angles, e.g., ±45°. To provide for normalization of such polarization information, difference signals, e.g., the difference of the signals representative of the two polarization images at the two different quarter wave plate angles, and/or ratio signals, e.g., the ratio of the signals representative of the two polarization images at the two different quarter wave plate angles, are generated. The computer apparatus 90 uses the ratio and/or difference signal to search a look-up table generated to correlate film thickness (t) and/or index of refraction (n) with such ratio or difference signals.

Computer apparatus 90 runs software that allows the user to control the imaging ellipsometer apparatus 50 by means of a graphical user interface (not shown) to the apparatus 50. For example, computer apparatus 90 may be interfaced to the apparatus 50 through a microcontroller, rotation of components of the apparatus 50 may be controlled thereby, real time calculation of information regarding the sample may be generated from ellipsometry signals provided from the CCD detector 86, as well as other functionality may be provided for with use of the computer apparatus 90. For example, a software package such as commonly used Matlab or Labview may be used in the generation of images using the captured polarization information from CCD detector 86.

One skilled in the art will recognize that any number of polarization images may be captured by the CCD detector 86 and analyzed by computer apparatus 90. For example, additional images corresponding to different rotation angles of the quarter wave plate 80 may be captured. Further, for example, analyzer 82 may be rotated with the capturing of additional polarization images by the CCD detector 86 at various positions of the analyzer 82. Such capturing of additional images at different positions of the quarter wave plate 80 and/or the analyzer 82 may be used to improve signal to noise ratio and accuracy.

Figure 4:
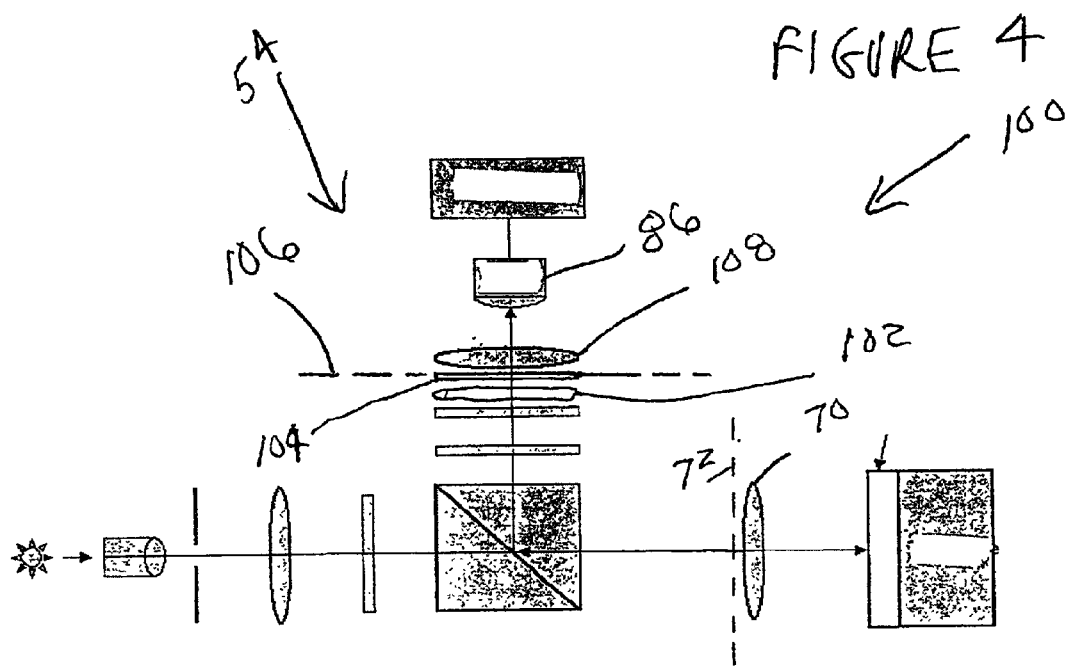
FIG. 4 is an alternate configuration of an imaging ellipsometer apparatus according to the present invention.

FIG. 4 shows an alternate imaging ellipsometer apparatus 100 which is substantially the same as that shown in FIG. 3 except that the spatial filter is repositioned in the analyzer arm 54 of the imaging ellipsometer apparatus 100. As such, reference numerals from FIG. 3 are used in the description of FIG. 4 for equivalent components with any new or repositioned components being renumbered.

As shown in FIG. 4, spatial filter 104, used in accordance with the present invention as described with reference to FIG. 3, may be placed at the conjugate plane 106 of the exit pupil of the objective lens 70. In addition to the spatial filter 104 being repositioned in the analyzer arm 54, an additional lens 102 is used to provide proper focusing of the diverted reflected light prior to the light passing through spatial filter 104 and being focused onto detector 86 via second lens 108.

Figure 5:
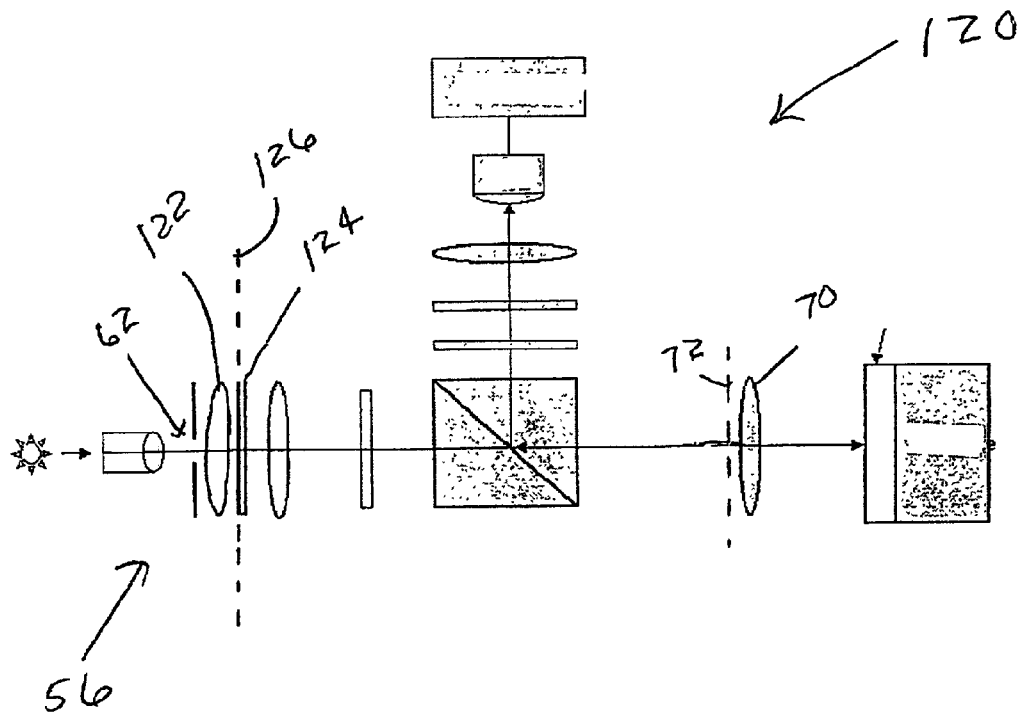
FIG. 5 is another alternate embodiment of an imaging ellipsometer apparatus according to the present invention.

Likewise, as shown in FIG. 5, imaging ellipsometer apparatus 120 is substantially the same as that shown in FIG. 3 except that the spatial filter is repositioned in the illumination source 56 of the imaging ellipsometer apparatus 120. As such, reference numerals from FIG. 3 are used in the description of FIG. 5 for equivalent components with any new or repositioned components being renumbered. The spatial filter 124 is positioned at the conjugate plane 126 of the exit pupil of objective lens 70. An additional lens 122 is positioned between pin hole opening 62 and the spatial filter 124 to provide proper focusing.

Figure 6:
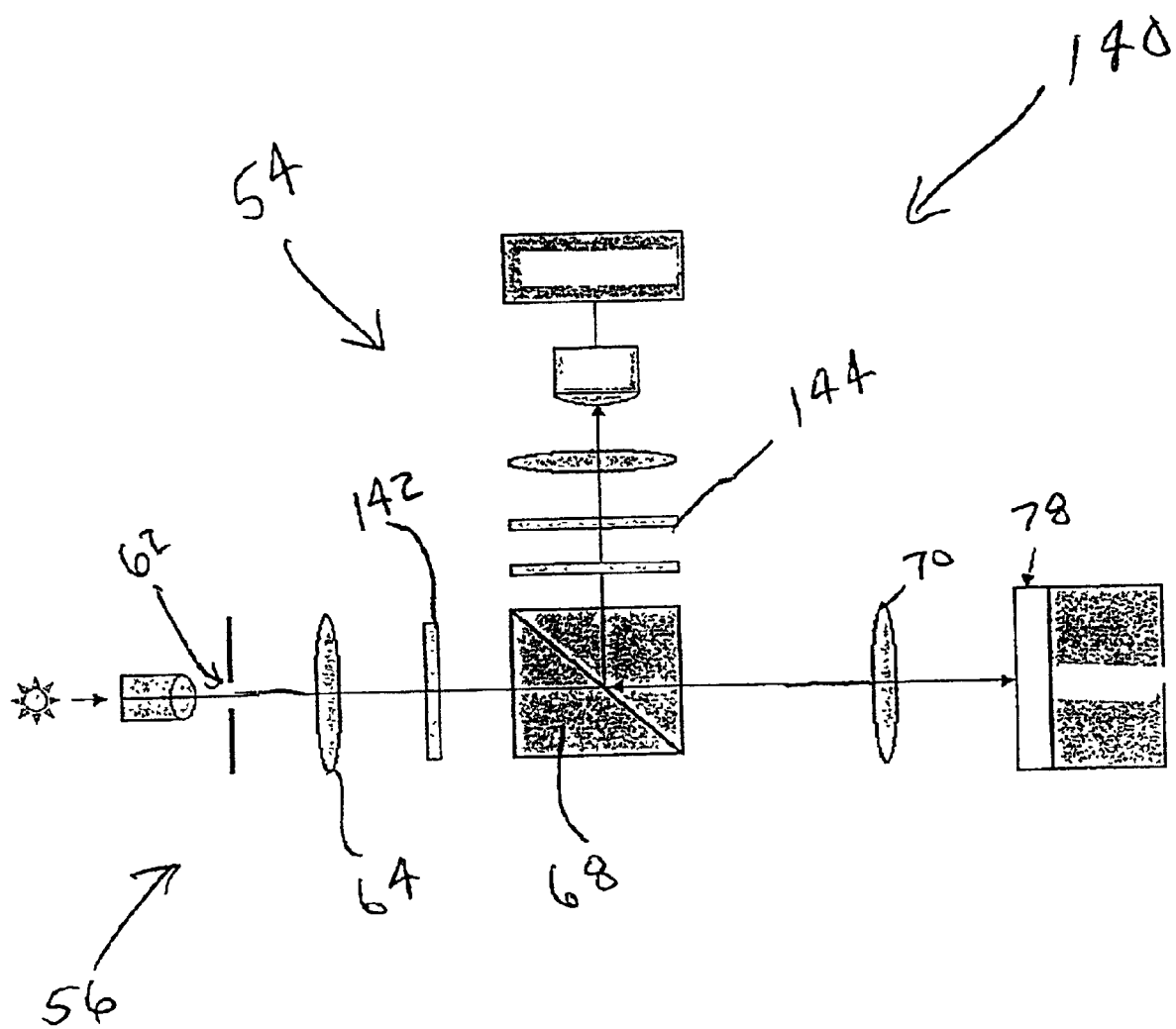
FIG. 6 is yet another alternate embodiment of an imaging ellipsometer apparatus according to the present invention.

FIG. 6 shows an alternate imaging ellipsometer apparatus 140 which is substantially the same as that shown in FIG. 3 except that the spatial filter 74 and the linear polarizer 66 are replaced with a polarization converter 142 to take advantage of the use of light with polarization states that are at ±45° with respect to the light's incident plane. As such, reference numerals from FIG. 3 are used in the description of FIG. 6 for equivalent components with any new or repositioned components being renumbered. Accordingly, imaging ellipsometer apparatus 140 includes a polarization converter 142 in the illumination source 56, positioned between lens 64 and beam splitter 68 to illuminate objective lens 70 with light having polarization states that are at ±45° with respect to the incident plane thereof. Likewise, a matched analyzer 144, i.e., crossed at 90° relative to the polarization converter 142, is used in the analyzer arm 54. Note that the polarization converter 142 breaks the symmetry of the phase information of the reflected light performing the function of the spatial filter 74.

Figure 9:
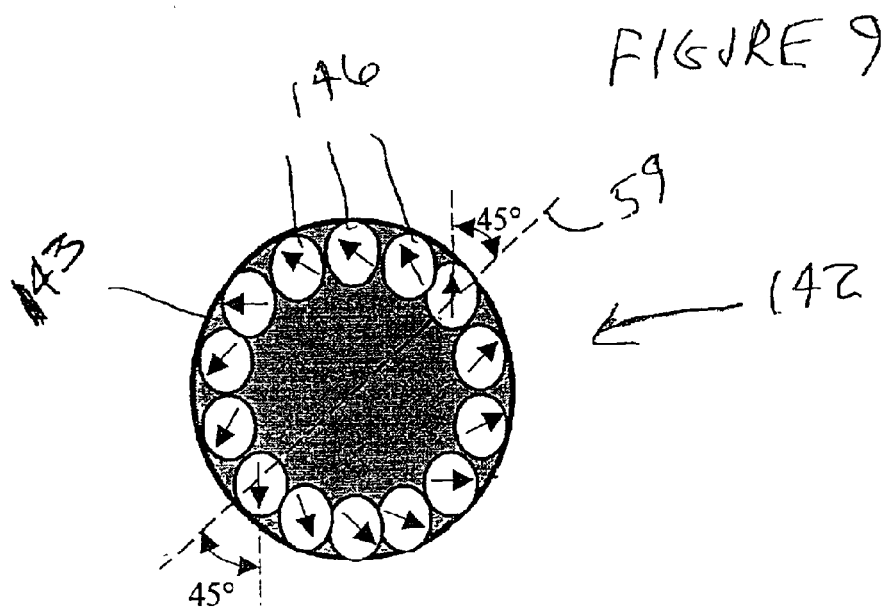
FIG. 9 is a diagram showing an illustrative embodiment of a polarization converter for use in the imaging ellipsometer apparatus described with reference to FIG. 6.

One graphical illustration of an embodiment of a polarization converter 142 is shown in FIG. 9. The polarization converter 142 includes an aperture mask 143 including polarization elements 146 in an annular region at the perimeter thereof The arrows in the polarization elements 146 indicate the transmission axis of the local polarization performed by the polarization converter 142. As shown, the polarization states of the light are at 45° relative to the incident plane 59 of the light in the imaging ellipsometer apparatus 140. The use of the polarization converter 142 and the matching analyzer 144 provide enhanced signal to noise ratio.

Various ways may be used to create such a polarization converter 142. For example, the converter 142 may be made by fabricating subwavelength defractive optical structures using microelectronic fabrication. In addition, a converter 142 may be formed by patterning a liquid crystal cell structure to produce the desired polarization rotation.

Figure 10:
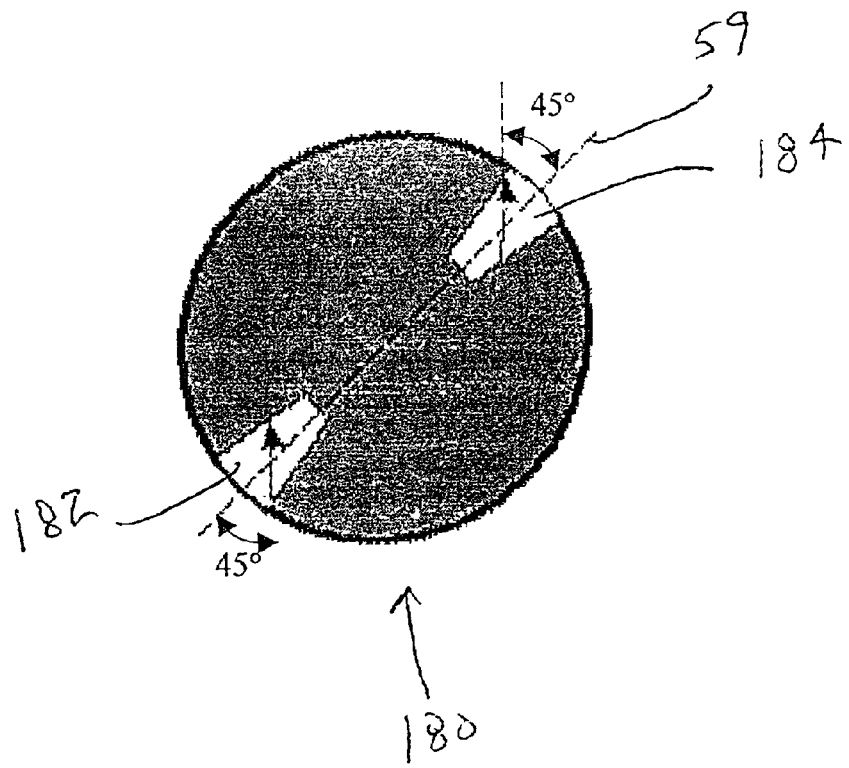
FIG. 10 is a diagram illustrating another alternate embodiment of a spatial filter for use in an imaging ellipsometer apparatus according to the present invention.
Figure 11:
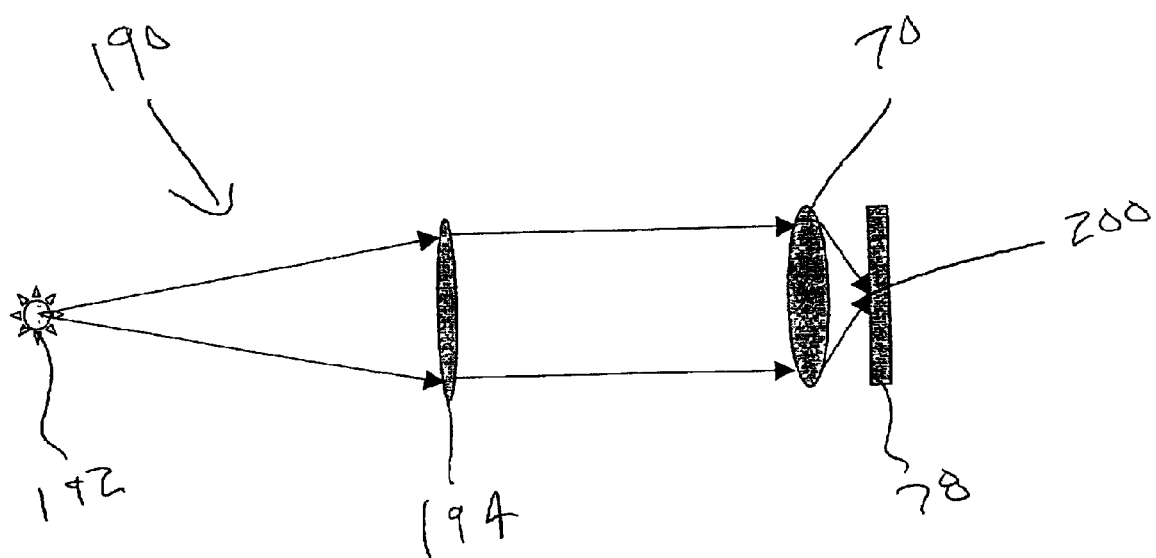
FIG. 11 is an illustration of an illumination technique for use in an imaging ellipsometer apparatus according to the present invention.

Another technique of providing improved signal-to-noise ratio is also based on the observation that polarization states at ±45° with respect to the incident plane give rise to maximum polarization rotation. This technique using a particular spatial filter 180 is represented in FIG. 10 and described with reference thereto in combination with FIG. 3. As such, reference numerals from FIG. 3 are used in the description of FIG. 10 for equivalent components with any new or repositioned components being renumbered.

Unlike the use of polarization conversion as described with reference to FIG. 9, this particular technique uses the spatial filter 180 at the plane of the exit pupil of the objective lens 70. The spatial filter 180 includes an aperture mask arranged such that the polarization state of the light that passes through the light passing portions 182, 184 of the spatial filter 180 are aligned at 45° with respect to the incident plane 59 of the light. As shown in FIG. 10, the aperture mask includes two polarization portions 182, 184 positioned in opposing relation to one another at the perimeter of the aperture mask. Generally, such portions 182, 184 may take any number of shapes as long as suitable polarization is accomplished. As a result, the output signal from the imaging ellipsometer apparatus 50 is maximized.

The aperture mask of the spatial filter 180 performs spatial frequency sampling. If only a single polarization image is used in this embodiment to produce an image of the sample 76, many spatial frequency components may be lost, leading to degradation of the resulting mapped image. However, by rotating the polarizer 66, the spatial filter 180, and the analyzer 82, in a synchronous manner, a sequence of images can be detected and attained Although these images may be low resolution polarization images, the polarization images may be summed in a suitably designed digital filter and used to reconstruct an image with higher resolution. Such reconstruction is performed by computer apparatus 90 and suitable software running thereon designed for performing such digital reconstruction.

To further attempt to eliminate problems of degradation of resolution in one or more of the previous embodiments of the imaging ellipsometer apparatus, particularly with regard to the embodiment described with reference to FIG. 10, a spatial sampling technique can also be used to reduce such degradation. The spatial sampling technique, is at least partly shown in FIG. 11, and includes a special illumination system 190 used in an imaging ellipsometer apparatus described herein. The illumination system 190 illuminates only a thin line 200 on the film 78 of sample 76. Preferably, the width of the thin line is on the order of the resolution of the objective lens 70. The spatial filter 74 and the thin line are oriented in parallel to one another. In one embodiment, the illumination system 190 includes a thin filament bulb source 192 for providing light incident on a low numerical aperture lens 194. For example, the low numerical aperture lens 194 may have a numerical aperture in the range of less than 0.2. With such an illumination system 190 providing light to the high numerical aperture objective lens 70, as shown in the imaging ellipsometer apparatus 50 of FIG. 3, an image of the filament is projected onto the sample 78 by the objective lens 70 as line 200. In this way, the information from the illuminated thin line 200 on the sample 78 can be reflected and analyzed. Under control of the computer apparatus 90 and any other system components required, this illuminated line 200 may be swept across the sample 78 to achieve a diffraction limited image.

One that is skilled in the art will recognize that with use of a multiple wavelength source and suitable analysis tools, spectroscopic ellipsometry may be performed using the concepts as described above.

Further, in accordance with the present invention, by imaging a large area at one time with high resolution, the imaging ellipsometer apparatus 50 is much faster than a point-by-point scan of the sample with a conventional ellipsometer. It can follow dynamic phenomena in real-time. However, in many circumstances, it may be required to provide even higher resolution and information with regard to a much smaller area, e.g., a spot, of the sample 76. As such, a spot ellipsometer apparatus as described in copending U.S. patent application Ser. No. 09/691,346, entitled "Ellipsometer Using Radial Symmetry," may be used to provide such information. This co-pending application is hereby incorporated in its entirety by reference hereto. It will be recognized that various components of the imaging ellipsometry apparatus as described herein may be used in a spot ellipsometer apparatus as described in the co-pending application. For example, the same objective lens may be used commonly by both the imaging ellipsometer apparatus according to the present invention and the ellipsometer for providing information with regard to a spot, as described in the co-pending application entitled "Ellipsometer Using Radial Symmetry." For example, modular components may be replaced in the apparatus depending upon which ellipsometer is being required. Further, other common components may exist such that they can be used in a modular manner between the two apparatus.

All patents and references disclosed herein are incorporated by reference in their entirety, as if individually incorporated. Further, although the present invention has been described with particular reference to various embodiments thereof, variations and modifications of the present invention can be made within the contemplated scope of the following claims, as is readily known to one skilled in the art.

What is claimed is:

1. An ellipsometer apparatus for use in providing an image of at least a portion of a sample, the ellipsometer apparatus comprising:

an objective lens having a focal plane at which a sample plane of the sample is positioned;

an illumination source for providing incident light normal to the sample plane, wherein the incident light comprises linearly polarized light incident on the objective lens, wherein the linearly polarized light comprises p and s wave components, wherein the objective lens focuses the incident linearly polarized light onto the sample, and further wherein at least a portion of the focused incident polarized light is reflected by the sample resulting in reflected light, the reflected light comprising p and s wave components corresponding, respectively, to the p and s wave components of the incident light focused on the sample;

a spatial filter to modify at least a portion of the incident light or the reflected light, wherein the spatial filter is positioned at a plane of an exit pupil of the objective lens; and an analyzer portion for use in resolving a polarization state of the reflected light, and further wherein the analyzer portion is operable to generate polarization information based on the reflected light, wherein the polarization information is a function of the p and s wave components of the incident light having different reflectivities from the sample.

2. The apparatus of claim 1, wherein the illumination source comprises a fiber illuminator.

3. The apparatus of claim 2, wherein the fiber illuminator comprises a light source and a fiber bundle.

4. The apparatus of claim 1, wherein the objective lens is a high numerical aperture objective lens having an numerical aperture in the range of 0.5 to less than 1.

5. The apparatus of claim 1, wherein the spatial filter is positioned adjacent the objective lens in an actual plane of the exit pupil thereof.

6. The apparatus of claim 1, wherein the spatial filter is part of the illumination source and is positioned in a conjugate plane of the exit pupil of the objective lens.

7. The apparatus of claim 1, wherein the spatial filter is part of the analyzer portion and is positioned in a conjugate plane of the exit pupil of the objective lens.

8. The apparatus of claim 1, wherein the analyzer portion comprises:

a rotatable quarter wave plate;

an analyzer;

a lens; and a detector, wherein the rotatable quarter wave plate, the analyzer, and the lens are positioned such that the reflected light passes through the rotatable quarter wave plate and the analyzer, and further wherein the reflected light is focused onto the detector by the lens.

9. The apparatus of claim 8, wherein the detector is a charge coupled device array detector.

10. The apparatus of claim 1, wherein the apparatus further comprises a beam splitter for passing the linearly polarized light normal to the sample plane and incident on the objective lens, and further wherein the beam splitter diverts the reflected light to the analyzer portion.

11. The apparatus of claim 1, wherein the illumination source comprises a polarization converter providing for linearly polarized light with polarization states that are at +/−45 degrees with respect to an incident plane of the linearly polarized light, and wherein the analyzer portion comprises a polarization device matched to the polarization converter of the illumination source.

12. The apparatus of claim 1, wherein the spatial filter is configured such that the polarization state of the light that is modified thereby is aligned at 45 degrees with respect to an incident plane of the linearly polarized light.

13. The apparatus of claim 1, wherein the illumination source includes a thin filament bulb and a low numerical aperture lens for use in projecting an image of the filament onto the sample and is operable to sweep the image across the sample.

14. The apparatus of claim 1, wherein the spatial filter is operable to break the azimuth symmetry of the incident light or the reflected light.

15. An ellipsometry method for use in providing an image of at least a portion of a sample, the method comprising:

providing an objective lens having a focal plane at which a sample plane of the sample is positioned;

providing linearly polarized light normal to the sample plane incident on the objective lens, wherein providing linearly polarized light comprises providing p and s wave components;

focusing the incident linearly polarized light onto the sample, wherein at least a portion of the focused incident polarized light is reflected by the sample resulting in reflected light, wherein the reflected light comprises p and s wave components corresponding, respectively, to the p and s wave components of the incident light focused on the sample;

spatial filtering at least a portion of the incident light or the reflected light using a spatial filter positioned at a plane of an exit pupil of the objective lens; and generating polarization information based on the reflected light for use in resolving a polarization state of the reflected light, wherein the polarization information is a function of the p and s wave components of the incident light having different reflectivities from the sample.

16. The method of claim 15, wherein providing linearly polarized light normal to the sample plane incident on the objective lens comprises:

providing light from an extended source;

collimating the light; and linearly polarizing the collimated light.

17. The method of claim 15, wherein the objective lens is a high numerical aperture objective lens having a numerical aperture in the range of 0.5 to less than 1.

18. The method of claim 15, wherein spatial filtering at least a portion of the incident light or the reflected light comprises using a spatial filter at an actual plane of the exit pupil of the objective lens.

19. The method of claim 15, wherein spatial filtering at least a portion of the incident light or the reflected light comprises using a spatial filter at a conjugate plane of the exit pupil of the objective lens.

20. The method of claim 15, wherein generating polarization information based on the reflected light comprises:

passing the reflected light through an analyzer portion comprising at least a rotatable quarter wave plate and an analyzer;

rotating at least the rotatable quarter wave plate to at least two angular positions;

detecting at least two polarization images corresponding to the at least two angular positions.

21. The method of claim 20, wherein generating polarization information based on the reflected light further comprises generating an image using at least one of a ratio and a difference of the at least two polarization images.

22. The method of claim 20, wherein the method further comprises:
rotating the analyzer of the analyzer portion to one or more positions; and
generating additional polarization images corresponding to the one or more positions.

23. The method of claim 15, wherein providing linearly polarized light normal to the sample plane incident on the objective lens comprises providing linearly polarized light with polarization states that are at +/−45 degrees with respect to an incident plane of the linearly polarized light using a polarization converter, and further wherein generating polarization information based on the reflected light comprises generating polarization information based on the reflected light using a polarization device matched to the polarization converter.

24. The method of claim 15, wherein spatial filtering at least a portion of the incident light or the reflected light comprises providing a spatial filter configured such that the polarization state of the light that is modified thereby is aligned at 45 degrees with respect to an incident plane of the linearly polarized light incident on the objective lens.

25. The method of claim 24, wherein generating polarization information based on the reflected light comprises:
passing the reflected light through an analyzer portion comprising at least a rotatable quarter wave plate and an analyzer; and
synchronously rotating the rotatable quarter wave plate, the analyzer, and the spatial filter to obtain a plurality of polarization images.

26. The method of claim 15, wherein providing linearly polarized light normal to the sample plane incident on the objective lens comprises providing light such that an illumination line is focused on the sample, and further wherein the method comprises sweeping the illumination line across the sample.

27. An ellipsometer apparatus for use in providing an image of at least a portion of a sample, the ellipsometer apparatus comprising:
an objective lens having a focal plane at which a sample plane of the sample is positioned;
an illumination source comprising an extended light source for providing incident light normal to the sample plane, wherein the incident light comprises p and s wave components, wherein the incident light comprises linearly polarized light incident on the objective lens, wherein the objective lens focuses the incident linearly polarized light onto the sample, and further wherein at least a portion of the focused incident polarized light is reflected by the sample resulting in reflected light, the reflected light comprising p and s wave components corresponding, respectively, to the p and s wave components of the incident light focused on the sample;
a spatial filter to modify at least a portion of the incident light or the reflected light, wherein the spatial filter is operable to break the azimuth symmetry of the incident light or the reflected light; and
an analyzer portion for use in resolving a polarization state of the reflected light, wherein the analyzer portion is operable to generate polarization information based on the reflected light for use in generating an image of at least a portion of the sample using the polarization information, wherein the polarization information is a function of the p and s wave components of the incident light having different reflectivities from the sample.

28. The apparatus of claim 27, wherein the extended light source comprises a light source and a fiber bundle.

29. The apparatus of claim 27, wherein the spatial filter is positioned adjacent the objective lens in an actual plane of an exit pupil thereof.

30. The apparatus of claim 27, wherein the spatial filter is part of the illumination source and is positioned in a conjugate plane of an exit pupil of the objective lens.

31. The apparatus of claim 27, wherein the spatial filter is part of the analyzer portion and is positioned in a conjugate plane of an exit pupil of the objective lens.

32. The apparatus of claim 27, wherein the analyzer portion comprises:
a rotatable quarter wave plate,
an analyzer;
a lens; and
a detector, wherein the rotatable quarter wave plate, the analyzer, and the lens are positioned such that the reflected light passes through the rotatable quarter wave plate and the analyzer, and further wherein the reflected light is focused onto the detector by the lens.

33. The apparatus of claim 27, wherein the illumination source comprises a polarization converter providing for linearly polarized light with polarization states that are at +/−45 degrees with respect to an incident plane of the linearly polarized light, and wherein the analyzer portion comprises a polarization device matched to the polarization converter of the illumination source.

34. The apparatus of claim 27, wherein the spatial filter is configured such that the polarization state of the light that is modified thereby is aligned at 45 degrees with respect to an incident plane of the linearly polarized light.

35. An ellipsometry method for use in providing an image of at least a portion of a sample, the method comprising:
providing an objective lens having a focal plane at which a sample plane of the sample is positioned;
providing linearly polarized light normal to the sample plane incident on the objective lens, wherein providing linearly polarized light comprises providing light from an extended light source, and further wherein the linearly polarized light comprises p and s wave components;
focusing the incident linearly polarized light onto the sample, wherein at least a portion of the focused incident polarized light is reflected by the sample resulting in reflected light, wherein the reflected light comprises p and s wave components corresponding, respectively, to the p and s wave components of the incident light focused on the sample;
spatial filtering at least a portion of the incident light or the reflected light, wherein spatial filtering at least a portion of the incident light or reflected light comprises breaking the azimuth symmetry of the incident light or the reflected light;
generating polarization information based on the reflected light for use in resolving a polarization state of the reflected light, wherein the polarization information is a function of the p and s wave components of the incident light having different reflectivities from the sample; and
providing an image of at least a portion of the sample using the polarization information.

36. The method of claim 35, wherein providing linearly polarized light normal to the sample plane incident on the objective lens further comprises:
collimating the light provided by the extended light source; and
linearly polarizing the collimated light.

37. The method of claim 35, wherein spatial filtering at least a portion of the incident light or the reflected light comprises using a spatial filter at an actual plane of an exit pupil of the objective lens.

38. The method of claim 35, wherein spatial filtering at least a portion of the incident light or the reflected light comprises using a spatial filter at a conjugate plane of an exit pupil of the objective lens.

39. The method of claim 35, wherein generating polarization information based on the reflected light comprises:

passing the reflected light through an analyzer portion comprising at least a rotatable quarter wave plate and an analyzer;

rotating at least the rotatable quarter wave plate to at least two angular positions; and detecting at least two polarization images corresponding to the at least two angular positions.

40. The method of claim 39, wherein generating the image comprises generating the image of at least a portion of the sample using at least one of a ratio and a difference of the at least two polarization images.

41. The method of claim 40, wherein the method further comprises:

rotating the analyzer of the analyzer portion to one or more positions; and generating additional polarization images corresponding to the one or more positions.

42. The method of claim 35, wherein providing linearly polarized light normal to the sample plane incident on the objective lens comprises providing linearly polarized light with polarization states that are at +/−45 degrees with respect to an incident plane of the linearly polarized light using a polarization converter, and further wherein generating polarization information based on the reflected light comprises generating polarization information based on the reflected light using a polarization device matched to the polarization converter.

43. The method of claim 35, wherein spatial filtering at least a portion of the incident light or the reflected light comprises providing a spatial filter configured such that the polarization state of the light that is modified thereby is aligned at 45 degrees with respect to an incident plane of the linearly polarized light incident on the objective lens.

44. The method of claim 43, wherein generating polarization information based on the reflected light comprises:

passing the reflected light through an analyzer portion comprising at least a rotatable quarter wave plate and an analyzer; and synchronously rotating the rotatable quarter wave plate, the analyzer, and the spatial filter to obtain a plurality of polarization images.

* * * * *